United States Patent [19]

Teillaud et al.

[11] Patent Number: 5,605,702
[45] Date of Patent: Feb. 25, 1997

[54] EVA-BASED TRANSDERMAL MATRIX SYSTEM FOR THE ADMINISTRATION OF AN ESTROGEN AND/OR A PROGESTOGEN

[75] Inventors: Eric Teillaud, Talant; Antoine Sawaya, Dijon; Marie-Christine Math, Talant, all of France

[73] Assignee: Laboratoires d'Hygiene et de Dietetique, Paris, France

[21] Appl. No.: 413,208

[22] Filed: Mar. 28, 1995

[30] Foreign Application Priority Data

Mar. 28, 1994 [FR] France ................... 94 03598

[51] Int. Cl.⁶ .................................................. A61F 13/00
[52] U.S. Cl. ........................ 424/448; 424/449; 514/946
[58] Field of Search ................................. 424/448, 449; 514/946

[56] References Cited

U.S. PATENT DOCUMENTS

| | | | |
|---|---|---|---|
| 4,060,084 | 11/1977 | Chandrasekaran et al. | 128/260 |
| 4,752,612 | 6/1988 | Saito | 514/420 |
| 4,994,267 | 2/1991 | Sablotsky | 424/78 |
| 5,032,402 | 7/1991 | Digenis | 424/448 |

FOREIGN PATENT DOCUMENTS

| | | |
|---|---|---|
| 0371496 | 6/1990 | European Pat. Off. . |
| 0483370 | 5/1992 | European Pat. Off. . |
| 2612785 | 9/1988 | France . |

*Primary Examiner*—D. Gabrielle Phelan
*Attorney, Agent, or Firm*—Evenson, McKeown, Edwards & Lenahan, P.L.L.C.

[57] ABSTRACT

The present invention relates to a new self-adhesive transdermal matrix system for the administration of a hormone by percutaneous route, said system which comprises a support and self-adhesive matrix, having a matrix comprising:

(a) 40 to 60 parts by weight of an ethylene/vinyl acetate copolymer, (b) 5 to 20 parts by weight of a cellulosic material, (c) 35 to 55 parts by weight of at least one compound selected from the group consisting of: crotamiton, N-substituted 2-pyrrolidones of the formula I,

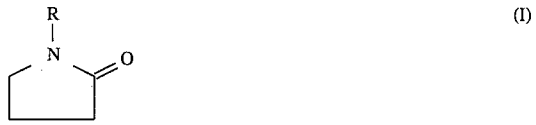

(I)

in which the R group represents a $(C_1-C_{15})$-alkyl, cyclohexyl or 2-hydroxyethyl group, and higher $C_{12}-C_{20}$ aliphatic alcohols, and (d) 0,01 to 7 parts by weight of a hormone selected from the group consisting of estrogen components, progestogen components and mixtures thereof.

It also relates to a method for preparing this transdermal matrix system.

29 Claims, 2 Drawing Sheets

EVA-BASED TRANSDERMAL MATRIX SYSTEM FOR THE ADMINISTRATION OF AN ESTROGEN AND/OR A PROGESTOGEN

FIELD OF THE INVENTION

This invention is concerned with a new self-adhesive matrix system for the administration of an oestrogen component and/or a progestogen component by percutaneous route, based on a copolymer of ethylene and vinyl acetate (EVA).

PRIOR ART

It is known that numerous transdermal systems for the administration of an estrogen component alone or in association with a progestogen component have been investigated over the last decade, in particular for the treatment of symptoms of the menopause and osteoporosis within the framework of treatments described as "hormone deficiency replacement therapy". Matrix systems whose matrix is based on a copolymer of ethylene and vinyl acetate (EVA) and in which the active ingredients are dispersed or dissolved are described especially in patent document FR-A-2 612 785 and, regarding the administration of an estrogen-progestogen combination, in patent documents EP-A-0 279 982 and EP-A-0 555 360.

It is also known by persons skilled in the art that, for EVAs as in general for all polymers used in transdermal systems, it is impossible, depending upon the nature of the compounds associated with the latter and the type of active ingredient used, to foresee the quantities of active ingredient released over time and the yields of these systems.

This is well illustrated by the examples of document FR-A-2 635 979 which describe EVA-based devices containing different active ingredients and which show that the results obtained are most variable.

In practice it is considered that only close active ingredients, that is to say belonging to the same chemical family, dissolved in identical formulations generally offer comparable properties. It is also known that oestrogens and progestogens are products which (i) are little soluble in EVA-type polymers and (ii) which cross the cutaneous barrier with difficulty.

Therefore the quantities of these active ingredients that are released to obtain the desired therapeutic effect are generally low compared with the initial quantities present in the transdermal devices, with the consequence that yields obtained are low.

AIMS OF THE INVENTION

According to the invention self-adhesive matrix systems are proposed for the administration of estrogens and/or progestogens which do not have the previously mentioned disadvantages and which also offer excellent yields.

According a first aspect of the invention, it is proposed to provide a transdermal matrix system based on EVA and a cellulose derivative for the administration of an oestrogen component and/or a progestogen component.

According to a second aspect of the invention, it is proposed to provide a process for preparation of such a matrix system.

OBJECT OF THE INVENTION

The above-mentioned purposes are achieved with a new technical solution according to which the matrix in the matrix system, which contains an estrogen component and/or a progestogen component, is composed substantially of an EVA material selected, a cellulosic material and a third product from selected from crotamiton, N-substituted 2-pyrrolidones of the formula I below, higher ($C_{12}$–$C_{20}$)-aliphatic alcohols and mixtures thereof.

To be more precise, a self-adhesive transdermal matrix system is proposed according to the invention for the administration of a hormone by percutaneous route, said system, which comprises a support and self-adhesive matrix, having a matrix comprising:

(a) 40 to 60 parts by weight of an ethylene/vinyl acetate copolymer, (b) 5 to 20 parts by weight of a cellulosic material, (c) 35 to 55 parts by weight of at least one compound selected from the group consisting of: crotamiton, N-substituted 2-pyrrolidones of the formula I,

in which the R group represents a ($C_1$–$C_{15}$)-alkyl, cyclohexyl or 2-hydroxyethyl group, and higher $C_{12}$–$C_{20}$ aliphatic alcohols, and (d) 0,01 to 7 parts by weight of a hormone selected from the group consisting of estrogen components, progestogen components and mixtures thereof.

According to the invention a method is also provided for prepararing said transdermal matrix system, comprising the steps consisting of, either:

(α) mixing the EVA and the cellulosic material while stirring at a temperature higher than 110° C.;

(β) incorporating into the resulting homogeneous mixture the hormone selected from the group consisting of oestrogen components, progestogen components and mixtures thereof, with the crotamiton and/or aliphatic alcohol when at least one of these products is required, under continued stirring at a temperature higher than 110° C., and then homogenizising;

(γ) incorporating into the resulting homogeneous mixture the N-substituted 2-pyrrolidone compound or compounds of the formula I, if they are required, while stirring at a temperature lower than 110° C., and homogenizing;

(δ) coating the homogeneous mixture resulting from step (β) or (γ) onto a temporary anti-adherent support at a temperature of between 100° and 140° C. in order to obtain a deposit of 50 to 300 g/m² on said support; and, (ε) transferring the matrix thus obtained onto a final support, or:

(α) successively incorporating, while stirring, the higher aliphatic alcohol, crotamiton and/or N-substituted 2-pyrrolidone(s) of the formula I (if one or several of these compounds are present in the formulation), the hormone selected from the group consisting of estrogen components, progestogen components and mixtures thereof, the EVA material, the cellulosic material and the chosen solvent;

(β) stirring the mixture thus obtained at a temperature lower than the boiling point temperature of the solvent until complete homogenization of said mixture;

(γ) coating the homogeneous mixture resulting from step (β) onto a temporary anti-adherent support at a temperature of between 50° and 70° C. in order to obtain a deposit of 50 to 300 g/m² on said support;

(δ) heating the coating thus obtained to evaporate the solvent at a temperature of between 40° and 80° C. in accordance with the boiling point of the latter; and, (ε) transferring the dry matrix thus obtained onto a final support,

BRIEF DESCRIPTION OF THE DRAWINGS

The appended FIGS. 1–4 illustrate the quantity of hormone released in time for the products according to the invention compared with a previously known transdermal system marketed under the tradename ESTRAGEST® by the company CIBA-GEIGY (here referenced E), in which:

FIG. 1: represents the released quantity (Q) of 17-β-oestradiol in mg/cm² in relation to time (t) in hours with combined systems of oestrogen-progestogen type, curves 10,11,12 and E1 respectively representing the products of examples 10,11,12 according to the invention and the ESTRAGEST® device;

FIG. 2: represents the released quantity (Q) of NETA (norethisterone acetate) in mg/cm² in relation to time (t) in hours with combined systems of estrogen-progestogen type, curves 11,12 and E2 respectively representing the products of examples 11 and 12 according to the invention and the ESTRAGEST® device;

FIG. 3: represents the released quantity (Q) of NETA in mg/cm² in relation to time (t) in hours with devices according to the invention containing NETA as sole hormone, curves 1,2,3 and E3 respectively representing the products of examples 1, 2 and 3 according to the invention and the ESTRAGEST® device; and, FIG. 4: represents the released quantity (Q) of 17-β-oestradiol in mg/cm² in relation to time (t) in hours with devices according to the invention containing 17-β-estradiol as sole hormone, curves 4,5,6,7 and E4 respectively representing the products of examples 4, 5, 6 and 7 according to the invention and the ESTRAGEST® device;

DETAILED DESCRIPTION OF THE INVENTION

Figure 1:
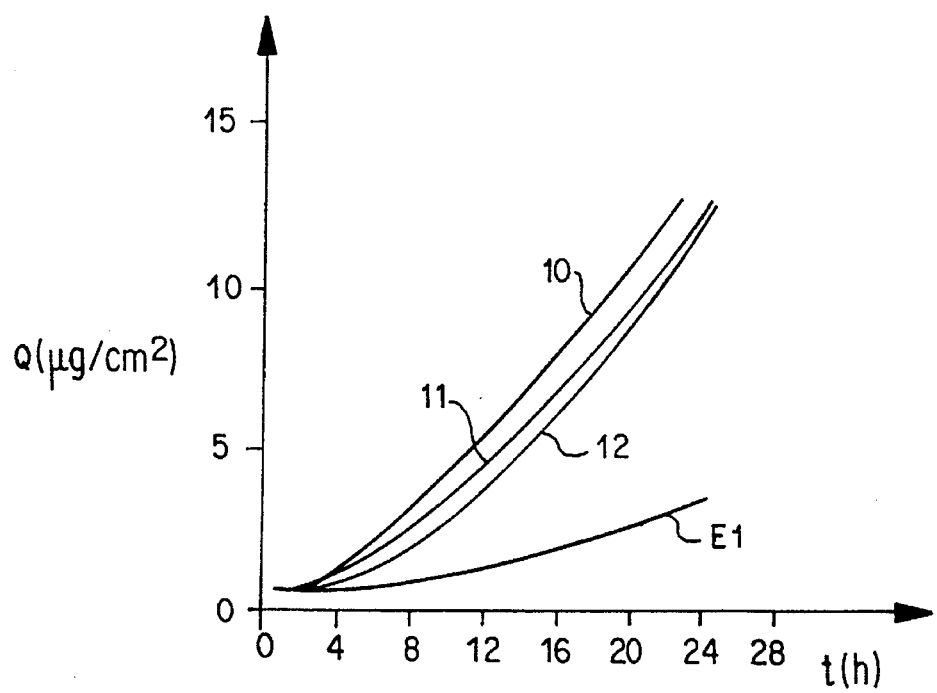

Preference is given to an ethylene/vinyl acetate copolymer whose vinyl acetate content lies between 30 and 75% by weight, in particular in the range of 45 to 60% by weight, with respect to the weight of the ethylene/vinyl acetate copolymer. A mixture of such EVAs may also be used having different molecular weights.

Among the higher aliphatic alcohols which are suitable according to the invention, mention is made of saturated or unsaturated monoalcohols having from. 12 to 20 carbon atoms, in particular 2-octyl-1-dodecanol, 1-hexadecanol, 1-octadecanol and 1-tetradecanol.

By a cellulosic material is meant here the alkylcelluloses such as for example methylcellulose, ethylcellulose, propylcellulose or methylpropylcellulose, and hydroxyalkylcelluloses such as, for example, hydroxymethylcellulose, hydroxyethylcellulose or hydroxypropylcellulose.

The N-substituted 2-pyrrolidones of formula I include here the substances in which the R group represents the cyclohexyl group, the 2-hydroxyethyl group or an alkyl group having from 1 to 15 carbon atoms, such as for example N-dodecyl-2-pyrrolidone, N-octyl-2-pyrrolidone, la N-methyl-2-pyrrolidone or N-ethyl-2-pyrrolidone.

Among the oestrogen components which are suitable according to the invention, particular mention can be made 17-β-estradiol, and the derivatives of estradiol, especially the mono- and di-esters of estradiol, such as for example estradiol 17-acetate, estradiol 3,17-diacetate, estradiol 3-benzoate, estradiol 17-undecanoate, alkyl derivatives at the 17 position of estradiol such as ethinyloestradiol, ethinyloestradiol 3-isopropylsulfonate, methyloestradiol, quinestrol, mestranol and, if need be, mixtures thereof.

Among the progestogen components which are suitable according to the invention particular mention can be made of progesterone, medrogesterone and their derivatives (especially 17-hydroxyprogesterone acetate, medroxyprogesterone acetate), norethisterone and its derivatives (especially 17-norethisterone acetate) and norpregnane.

According to the invention preference is given to 17-β-estradiol for the oestrogen component and to 17-norethisterone acetate (NETA) for the progestogen component.

The support for the matrix may be any support generally used for transdermal systems whether occlusive or not and impervious to the components of the matrix. For example preference may be given to a film support in polyethylene, polypropylene, polyester, a complex or composite consisting of polyethylene and a vinyl acetate/ethylene copolymer, or foams.

For practical purposes, the surface of the matrix, which is not attached to the support, may be covered by a protective layer or film which can be peeled off before using the device; said device can itself be packaged in a sealed protection, such as for example polyethylene-aluminium complexes.

Owing to the excellent yields of hormone release of the matrix system according to the invention, the latter offers numerous advantages that are described hereunder.

One advantage is the cost price which is substantially reduced compared with known device of the prior art, owing to the use of a lower quantity of hormone(s) whose price is high.

Also, the possibility of using less estrogens and/or progestogens while obtaining greater quantities of released product simplifies the development and production of formulations forming the matrix of the device.

Risks of polluting the environment with these hormones are also reduced when the product is discarded after treatment.

The problems connected with the solubility of the hormones in EVAs are therefore minimised or eliminated, as are the risks of chemical or physical incompatibility with the other constituents of the matrix. This also applies to problems of crystallization of the hormones and instability of the device, such phenomena being unacceptable for the approval and marketing of products intended for therapeutic purposes such as transdermal systems.

Finally, an important aspect of the invention is that these results are obtained without deteriorating the adhesive and cohesive properties of the matrix despite the use of significant quantities of products such as N-substituted 2-pyrrolidones of the formula I and the higher aliphatic alcohols. This is possible due to the presence of a cellulose derivative which acts as a cohesive agent and offsets the negative effects of said crotamiton, N-substituted 2-pyrrolidones of the formula I and higher aliphatic alcohols. If necessary, the adhesion and cohesion may also be optimised by using mixtures of EVAs of different molecular weights.

The transdermal systems according to the invention are made using the techniques generally used by persons skilled in the art: solvent phase coating or using the so-called "hot melt" technique, that is without the presence of a solvent.

In either case at industrial production level, large surface areas are coated and then cut to appropriate size with the dose of active ingredient to be administered over a given time.

For the so-called "hot melt" technique a method is provided which comprises the following steps:
 (1) the EVA is placed in a mixer while stirring at a temperature higher than 110° C., preferably at a temperature of 130° C., then the cellulosic material is added;
 (2) under continued stirring the active ingredient is then added gradually, followed by the higher aliphatic alcohol and/or the crotamiton (if either one or both are included in the formulation) and stirring is continued until complete homogenization of the mixture;
 (3) the N-substituted 2-pyrrolidone(s) of the formula I, which are more sensitive to heat are added at a temperature that is generally lower than the temperature for step (1), said temperature being determined in accordance with the thermal stability of these products, that is to say generally in the region of 100°–110° C., stirring is continued until a perfectly homogeneous mixture is obtained;
 (4) the homogeneous mixture thus obtained is coated, at a temperature of between 100° and 140° C., onto a temporary anti-adherent intermediate support, in particular a film of silicone polyester, to obtain a deposit of 50 to 300 g/m$^2$; and,
 (5) the matrix obtained at step (4) is then transferred to the chosen final support.

For the so-called "in solvent phase" technique a method is provided for the preparation of a self-adhesive matrix system according to the invention which comprises the following steps:
 (1) in a mixer are progressively incorporated, while stirring, the higher aliphatic alcohol, the crotamiton and/or the N-substituted 2-pyrrolidone(s) of the formula I (if one or several of these compounds are included in the formulation), the active ingredient(s), the EVA, the cellulosic material and the solvent, such as for example ethyl acetate;
 (2) the mixture obtained is stirred at a temperature of between 50° and 70° C. (lower than the boiling point temperature the chosen solvent) until full homogenization of the mixture;
 (3) the homogeneous mixture thus obtained is coated, at a temperature of between 50° and 70° C., onto a provisional anti-adherent intermediate support, more particularly silicone polyester film, to obtain a deposit of 50 to 300 g/m$^2$;
 (4) the solvent is evaporated by heating to a temperature of between 40° and 110° C., preferably 60° to 80° C., in accordance with the boiling point of the latter; and,
 (5) the dry matrix obtained at step (4) is transferred to the chosen final support.

The new self-adhesive matrix device according to the invention is particularly useful for the treatment of osteoporosis, symptoms of the menopause and resulting cardiovascular risks, in case of the so-called "hormone deficiency replacement therapy" and for any treatment requiring the administration of estrogen(s) and/or progestogen(s) by transdermal route.

BEST MODE

The best mode for carrying out the invention consisting of using a transdermal matrix system whose matrix contains per total 100 parts by weight: either,
 (a) 46 parts by weight of EVA,
 (b) 10 parts by weight of ethylcellulose,
 (c1) 31.5 parts by weight of 2-octyl-1-dodecanol,
 (c2) 10.5 parts by weight of N-dodecyl-2-pyrrolidone, and
 (d) 2 parts by weight of 17-β-estradiol, or,
 (a) 45 parts by weight of EVA,
 (b) 10 parts by weight of ethylcellulose,
 (c1) 30.75 parts by weight of 2-octyl-1-dodecanol,
 (c2) 10.25 parts by weight of N-dodecyl-2-pyrrolidone, and
 (d) 4 parts by weight of norethisterone acetate, or,
 (a) 42 parts by weight of EVA,
 (b) 15 parts by weight of ethylcellulose,
 (c1) 28 parts by weight of 2-octyl-1-dodecanol,
 (c2) 10 parts by weight of N-dodecyl-2-pyrrolidone,
 (d1) 2 parts by weight of 17-β-estradiol, and,
 (d2) 3 parts by weight of norethisterone acetate.

In these formulations, the EVA used ideally offers a vinyl acetate content of 35 to 60% by weight with respect to the weight of said EVA.

Other advantages and characteristics of the invention will be better understood on reading the description given below of examples and comparative assays.

These examples and assays are evidently by no means restrictive but are given by way of illustration.

For practical purposes, the following abbreviations are used in the description given below:
EVA: ethylene vinyl acetate copolymer
Es: 17-β-estradiol
NETA: norethisterone acetate

EXAMPLE 1

In a 250 ml beaker containing 40 g of ethyl acetate are added in fractions while stirring and heating to 60° C., 3 g of ETHOCEL® (ethylcellulose marketed by the company DOW CHEMICAL), then 6.75 g of ELVAX® 46L and 6.75 g of ELVAX® 46 (EVAs marketed by the company DU PONT). Stirring is continued for at least 30 minutes. While maintaining the temperature at 60° C. are added 12.34 g of SURFADONE® LP 300 (N-dodecyl-2-pyrrolidone marketed by the company GAF CORPORATION) et 1.2 g of NETA previously dissolved in 5 g of tetrahydrofuran. Stirring is continued for approximately 30 minutes at 60° C. then the mixture obtained is left to degas. This mixture is coated at 60° C. so as to form a deposit of (100±10) g/m$^2$ on a temporary support in silicone polyester. The coated product thus obtained is left at room temperature (15°–20° C.) for at least 15 hours so that the solvent evaporates. The matrix thus obtained is then transferred to a final support in polyethylene. It is cut to desired size and the products so cut are packed in thermosealable sachets.

A system is obtained in which the initial quantity of NETA is 400.3 μg/cm$^2$.

EXAMPLE 2

Procedure is identical to example 1, but using in this example 40 g of ethyl acetate, 3 g of ETHOCEL®, 6.75 g of ELVAX® 46L, 6.75 g of ELVAX® L, 10.8 g of EUTANOL® G (2-octyl-dodecanol marketed by the company HENKEL), 1.5 g of SURFADONE® LP 300 and 1.2 g of NETA dissolved in 5 g tetrahydrofuran. Coating is applied so as to obtain a matrix deposit of (100±10) g/m$^2$.

A system is obtained in which the initial quantity of NETA 400.3 µg/cm².

EXAMPLE 3

Procedure is identical to example 1, but using in this example 40 g of ethyl acetate, 2.96 g of ETHOCEL®, 6.75 g of ELVAX® 46L, 6.75 g of ELVAX® 46, 6.17 g of EUTANOL® G, 6.17 g of crotamiton [(N-ethyl-N-(2-methylphenyl)-2-butenamide, a product marketed by the company BOEHRINGER INGELHEIM)] and 1.2 g of NETA dissolved in 5 g of tetrahydrofuran. Coating is applied so as to obtain a matrix deposit of (100±10) g/m².

A system is obtained in which the initial quantity of NETA is 408.8 µg/cm².

EXAMPLE 4

Procedure is similar to example 1, but using in this example 3 g of ETHOCEL®, 6.87 g of ELVAX® 46L, 6.87 g of ELVAX® 46, 12.66 g of EUTANOL® G, 40 g of ethyl acetate and 0.6 g of 17-β-estradiol dissolved in 5 g of tetrahydrofuran. Coating is applied so as to obtain a matrix deposit of (100±10) g/m².

A system is obtained in which the initial quantity of 17-β-estradiol is 200 µg/cm².

EXAMPLE 5

Procedure is similar to example 4, but EUTANOL® G is replaced in this example by the same quantity of SURFADONE® LP 300. Coating is applied so as to obtain a matrix deposit of (100±10) g/m².

A system is obtained in which the initial quantity of 17-β-oestradiol is 200 µg/cm².

EXAMPLE 6

Procedure is similar to example 1, but using 3 g of ETHOCEL®, 6.87 g of ELVAX® 46L, 6.87 g of ELVAX® 46, 40 g of ethyl acetate, 11.16 g of EUTANOL® G, 1.5 g of SURFADONE® LP 300 and 0.6 g of 17-β-estradiol dissolved in 5 g of tetrahydrofuran. Coating is applied so as to obtain a matrix deposit of (100±10) g/m².

A system is obtained in which the initial quantity of 17-β-estradiol is 205.4 µg/cm².

EXAMPLE 7

Procedure is similar to example 1, but using in this example 3 g of ETHOCEL®, 6.87 g of ELVAX® 46L, 6.87 g of ELVAX® 46, 40 g of ethyl acetate, 6.33 g of EUTANOL® G, 6.33 g of crotamiton and 0.6 g of 17-β-estradiol dissolved in 5 g of tetrahydrofuran. Coating is applied so as to obtain a matrix deposit of (100±10) g/m².

A system is obtained in which the initial quantity of 17-β-estradiol is 200.2 µg/cm².

EXAMPLE 8

Procedure is similar to example 7 but the crotamiton is replaced in this example by the same quantity of SURFADONE® LP 300. Coating is applied so as to obtain a matrix deposit of (110±10) g/m².

A system is obtained in which the initial quantity of 17-β-oestradiol is 200 µg/cm²

EXAMPLE 9

Procedure is similar to example 1, but using 2.91 g of ETHOCEL®, 6.60 g of ELVAX® 46L, 6.60 g of ELVAX® 46, 12.09 g of EUTANOL® G, 40 g of ethyl acetate, 1.2 g of NETA and 0.6 g of 17-β-estradiol dissolved in 5 g of tetrahydrofuran. Coating is applied so as to obtain a matrix deposit of (100±10) g/m².

A system is obtained in which the initial quantity of NETA is 400 µg/cm² and the initial quantity of 17-β-estradiol is 200 µg/cm².

EXAMPLE 10

Procedure is identical to example 1, but using 2.9 g of ETHOCEL®, 6.60 g of ELVAX® 46L, 6.60 g of ELVAX® 46, 9.68 g of EUTANOL® G, 40 g of ethyl acetate, 2.42 g of SURFADONE® LP 300, and a solution of 1.2 g of NETA plus 0.6 g of 17-β-estradiol dissolved in 5 g of tetrahydrofuran. Coating is applied so as to obtain a matrix deposit of (100±10) g/m².

A system is obtained in which the initial quantity of NETA is 399.6 µg/cm² and the initial quantity of 17-β-estradiol is 200 µg/cm².

EXAMPLE 11

Procedure is similar to example 10, but in this example 2.42 of EUTANOL® G, and 9.68 g of SURFADONE® LP 300 are used respectively. Coating is applied so as to obtain a matrix deposit of (100±10) g/m².

A system is obtained in which the initial quantity of NETA is 400 µg/cm² and the initial quantity of 17-β-estradiol is 200 µg/cm².

EXAMPLE 12

Procedure is similar to example 10, but in this example 6.05 g of EUTANOL® G, and 6.05 g of SURFADONE® LP 300 are used respectively. Coating is applied so as to obtain a matrix deposit of (100±10) g/m².

A system is obtained in which the initial quantity of NETA is 400 µg/cm² and the initial quantity of 17-β-estradiol is 200 µg/cm².

EXAMPLE 13

Procedure is similar to example 6, but using 10.35 g of ELVAX® 46L, 3.45 g of ELVAX® 46, 3 g of ETHOCEL®, 40 g of ethyl acetate, 9,45 g of EUTANOL® G, 3.15 g of SURFADONE® LP 300, and 0.6 g of 17-β-estradiol dissolved in 5 g of tetrahydrofuran. Coating is applied so as to obtain a matrix deposit of (100±10) g/m².

A system is obtained in which the initial quantity of 17-β-oestradiol is 190.3 µg/cm².

EXAMPLE 14

Procedure is similar to example 2, but using 10.13 g of ELVAX® 46L, 3.38 g of ELVAX® 46, 3 g of ETHOCEL®, 40 g of ethyl acetate, 9.23 g of EUTANOL® G, 3.07 g of SURFADONE® LP 300, and 1.2 g of NETA dissolved in 5 g of tetrahydrofuran. Coating is applied so as to obtain a matrix deposit of (110±10) g/m².

A system is obtained in which the initial quantity of NETA is 466.7 µg/cm².

EXAMPLE 15

In a mixer are successively incorporated 130 g of SURFADONE® LP 300, 364 g of EUTANOL® G, 26 g of 17-β-estradiol, 39 g of NETA, 546 g of LEVAPREN® 450 P (an EVA copolymer containing 45% by weight of vinyl acetate, marketed by the company BAYER) and 195 g of ETHOCEL®. The mixture is gradually mixed and 1300 g of ethyl acetate are added. The mixture is heated to 65° C. while stirring until complete dissolution of the constituents, then the resulting mixture is left to degas. The mixture thus obtained is coated, at a temperature of between 50° and 60° C., onto a temporary silicone polyester support so that it forms a deposit of (100±10) g/m$^2$. The coating thus obtained is dried at a temperature of between 60° and 80° C. to evaporate the solvent. The matrix thus obtained is transferred onto a final support in polyethylene.

A system is obtained in which the initial quantity of 17-β-estradiol is 192 μg/cm$^2$ and the initial quantity of NETA is 291 μg/cm$^2$.

COMPARATIVE EXAMPLE CP1

A device of the type described in published document FR-A-2 612 785 is prepared.

In a 5 liter mixer are added 1610 g of LEVAPREN® 450 (EVA with a vinyl acetate motif content of 45% marketed by the company BAYER) and 1070 g of EUTANOL® G (2-octyldodecanol marketed by the company HENKEL). The mixture is heated to 140° C. and to it are added, in small fractions, 262.5 g of ETHOCEL® 20 (ethylcellulose with a viscosity of 2×10$^{-2}$ Pa.s). After homogenizing the medium, 540 g of EUTANOL® G are added. All the constituents are homogenized for 0.5 hour then left to stand for 24 hours. The mass is then heated to 60° C. for 0.5 hour and a solution of 5 g of dipropyleneglycol (DPG) and 175 g of 17-β-estradiol in 875 g of anhydrous ethanol is added. The mixture is homogenized for one hour without heating. This mass is coated onto a 105 mm wide silicone paper at a temperature of 60° C. to cellulosic material of (120±10) g/m$^2$. After heating the coated silicone paper to 80° C. to evaporate the ethanol, the matrix is transferred to a final support in polyethylene. This is cut to desired sizes which are packed in thermosealed aluminium/polyethylene sachets.

A system is obtained in which the initial quantity of 17-β-estradiol is 565 μg/cm$^2$.

The yields of the devices according to the invention are determined using measurements of the quantities of hormone(s) released in 24 hours on an ex vivo skin model.

For this purpose ex vivo permeation tests were carried out on the abdominal skin of male "nude" mice using the following protocol.

The measurement of the quantities of hormone(s) released by a transdermal apparatus with a surface area 2,54 cm$^2$, previously stamped out and deposited on a 3.14 cm$^2$ disk of abdominal skin from male "nude" mice, is carried out in a glass static cell with a thermostat setting of 37° C. having a receptor compartment with a volume of 11.5 ml, this receptor compartment containing a physiological saline solution/PEG$_{400}$ (75/25) (V/V) mixture, as a receptive phase.

Samples are taken from the receptive phase solutions at 2, 4, 6, 8, 12, 16, 20 and 24 hours, and they are titrated using liquid chromatography.

Taking into consideration the variability of results related to the intrinsic permeability of the skin samples, each permeation test for a transdermal apparatus sample was carried out on a minimum number of 3 to 5 skin samples.

The results, which are given, are the average obtained for each apparatus with these tests. The ratio between this average value of the quantities of hormone(s) released after 24 hour kinetics and the initial quantity of hormone(s) contained in the device is used to evaluate the yield at 24 hours of the transdermal device according to the invention.

For the comparison, the same method was used to determine the quantities of hormones released in 24 hours by the only product that is currently available and which comprises both an estrogen and a progestogen, namely the device marketed under the tradename ESTRAGEST® by the company CIBA-GEIGY. Moreover, it is the only marketed transdermal system which contains a progestogen component.

The ESTRAGEST® device consists of two reservoirs joined side by side containing a total of 10 mg of 17-β-estradiol and 30 mg of NETA, each reservoir containing a mixture of 5 mg of 17-β-estradiol and 15 mg of NETA.

The measurements of cutaneous permeation were taken using the same protocol on only one of the two reservoirs placed on a skin sample measuring 3.14 cm$^2$. The initial quantities of hormone(s) contained in this reservoir were reduced to the initial quantity of hormone(s) per unit surface area expressed in μg/cm$^2$.

The ratio between the average value of the quantities of 17-β-estradiol or NETA released in 24 hours and the initial quantity contained in the reservoir can be used to obtain the yields in 24 hours of 17-β-oestradiol or NETA.

The results obtained are given in tables I and II below.

Comparative ex vivo permeation assays were also made on the abdominal skin of male "nude" mice in relation to previously known matrix systems, in particular those described in the above-mentioned document FR-A-2 612 785.

In this case the measurements were made using the protocol described above but in order to comply with the operative conditions described in said document, a transdermal device according to the invention with a surface area of 2 cm$^2$ was applied and for the receptive phase a physiological saline solution/ethanol/PEG$_{400}$ (64/20/16) (V/V) mixture was used.

Also, in this case regular samples were taken up until 48 hours. The yields at both 24 and 48 hours were always calculated as the ratio between the average value of the quantity of 17-β-estradiol released and the initial quantity of 17-β-estradiol contained in the device of said document. This was comparative example 1 (CP1).

The results which were obtained are given in table III below.

In respect of a matrix containing both 17-β-estradiol and NETA, table I illustrates the advantages of the systems according to the invention compared with the above-mentioned ESTRAGEST® product.

Figure 2:
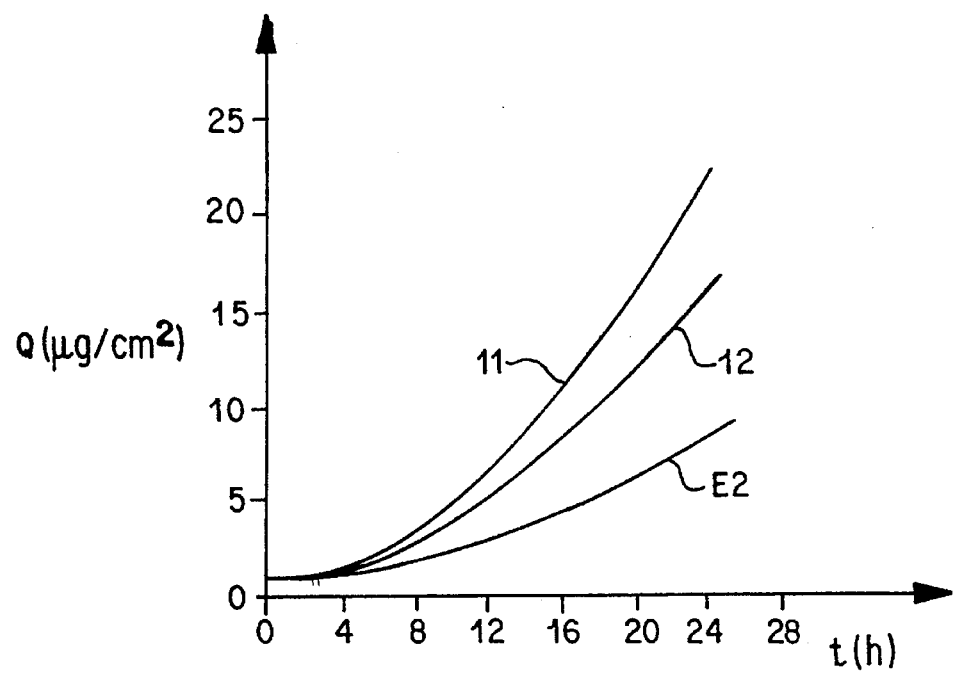
Figure 3:
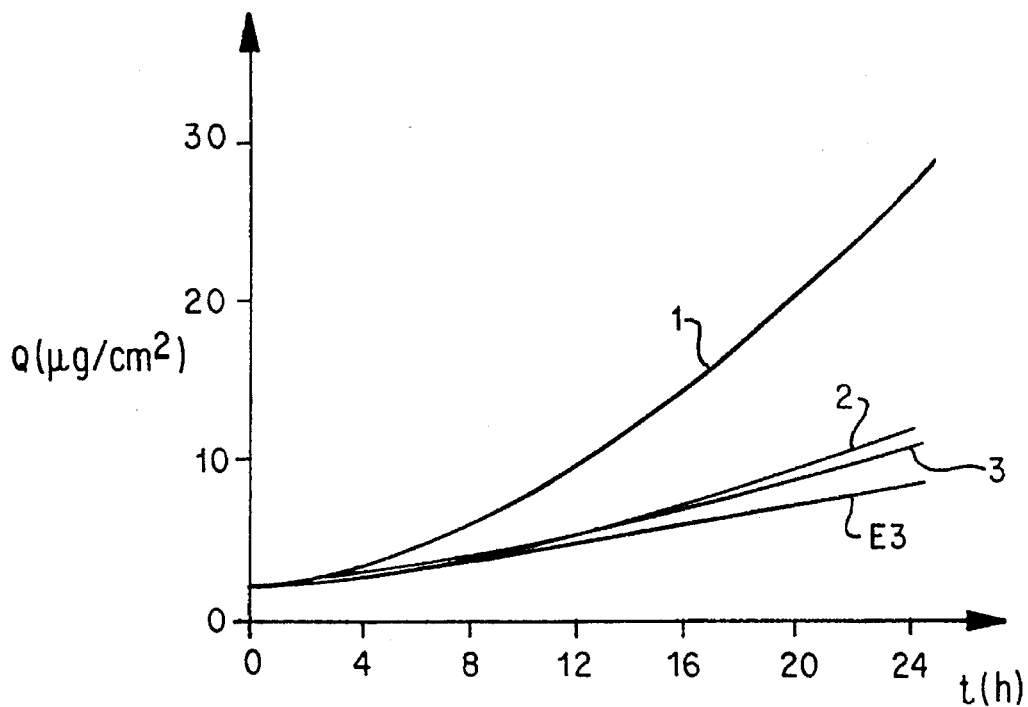

It is observed in this case that, as shown by curves (10–11), (11–12) and (1–2) in FIGS. 1 to 3, the quantities of hormones released by the device according to the invention both of 17-β-estradiol and of NETA are always significantly higher than those obtained with the ESTRAGEST® device, and these results are achieved with lower initial quantities, 8 and 12 times lower respectively.

Also, as shown by table I, the yields of 17-β-estradiol were on average 30 times higher than with ESTRAGEST® and NETA yields were 14 to 33 times higher than those of ESTRAGEST®.

These considerable differences again demonstrate the advantages of the invention which allow significant savings to be made by using less product for the desired therapeutic purpose, avoiding possible crystallization problems in the matrix, simplifying the development and producing smaller sized systems.

Figure 4:
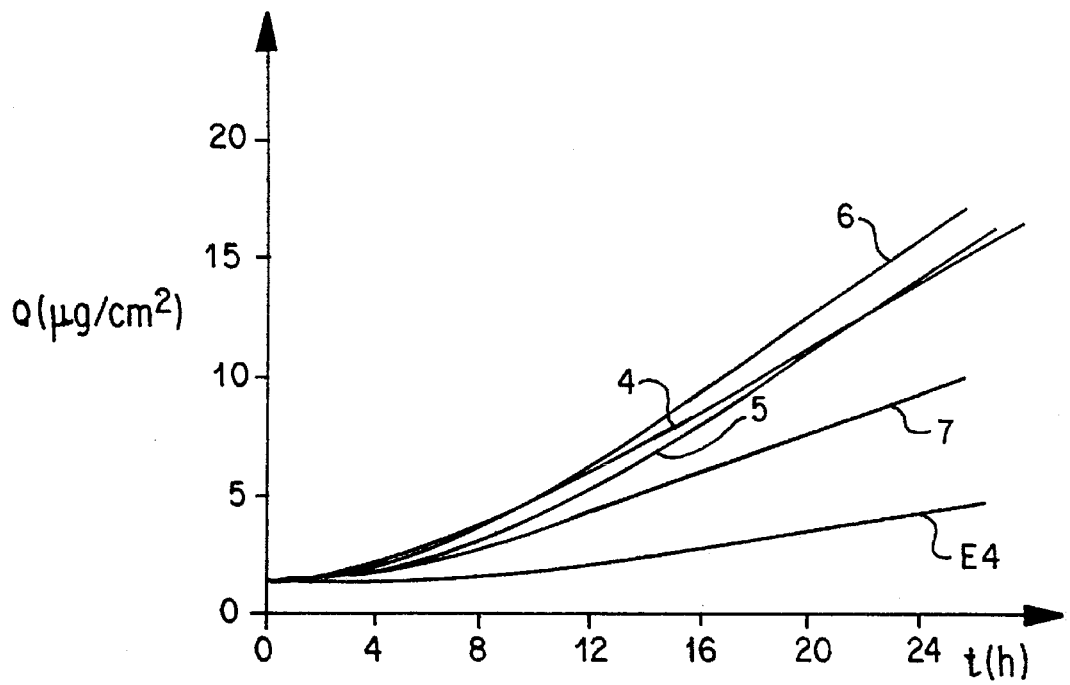

Also, similar results were obtained for those systems containing 17-β-estradiol alone or NETA alone, as is illustrated by FIGS. 3 and 4, firstly, and table II secondly.

FIG. 4 shows that for the products of examples 4, 5, 6 and 7 according to the invention, the quantities of 17-β-estradiol released during ex vivo cutaneous permeation tests on the abdominal skin of male "nude" mice were always higher than those released by ESTRAGEST®.

Also, FIG. 3 shows that in the case of NETA used alone in the matrix (examples 1, 2 and 3), in comparison with the NETA released by ESTRAGEST®, the device according to the invention always gave higher released quantities, in particular in the case of the product of example 1, even though concentrations were 12 times lower.

The results in table II show that the released quantities of 17-β-estradiol and NETA were always higher than with the ESTRAGEST® device.

The analysis of yields in table II shows that, compared with the ESTRAGEST® device, yields of 17-β-estradiol were respectively 33 times higher for the products of examples 4 and 5, 35 times higher for the product of example 6, and 21 times higher for the product of example 7.

Also, the yields of NETA were respectively 17 times, 16 times and even 42 times higher for the products of examples 2, 3 and 1.

When comparing ESTRAGEST® with the products of the other examples according to the invention, results are observed to be identical with those of table I.

The results of table III also indicate the advantages of the device according to the invention compared with the systems described in patent document FR-A-2 612 785, illustrated here by comparative example CP1.

It is again observed that the yields obtained with the products according to the invention are always higher. They are approximately 2 times higher at 24 hours and 1.7 times higher at 48 hours. Taking into consideration the variability of the results obtained with the chosen skin model, results are therefore comparable.

Finally, still using the abdominal skin of "nude" mice and the same protocol with a physiological saline solution/ $PEG_{400}$ (75/25) (V/V) mixture as receptive phase, measurements were made of the quantities released and yields at 24 hours with the device according to the invention in which the weight ratio between the two EVA polymers of the matrix was 3 (products of examples 13 and 14) and differed from the ratio of the previous examples which was always 1. Also a device according to the invention was used which only contains one EVA copolymer (example 15). The results obtained with the products of these 3 examples (Ex. 13–Ex. 15) compared with the ESTRAGEST® product are given in table IV.

It is again observed that, both with 17-β-estradiol alone (example 13), and with NETA alone (example 14), or with a mixture of these two hormones (examples 15), the quantities released in 24 hours and the yields at 24 hours were always of the same order as previously and were always much higher than with ESTRAGEST®. The figures are:

for example 13, a yield that is 27 times higher for 17-β-estradiol, for example 14, a yield that is 22 times higher for NETA, for example 15, a yield that is 20 times higher for NETA and 32 times higher for 17-β-estradiol

TABLE I

Comparison on abdominal skin of male "nude" mice.

| | Ex 9 | | Ex 10 | | Ex 11 | | Ex 12 | | ESTRAGEST ® | |
|---|---|---|---|---|---|---|---|---|---|---|
| | Es | NETA | Es | NETA | Es | NETA | Es | NETA | Es | NETA |
| $Q_0$ | 200 | 399.6 | 200 | 400.6 | 200 | 400 | 200.2 | 400 | 1604 | 4740 |
| $Q_{24}$ | 13.24 ± 2.2 | 8.99 ± 1.2 | 13.48 ± 1.5 | 11.86 ± 1.6 | 12.73 ± 2.6 | 21.58 ± 4.7 | 12.41 ± 0.6 | 15.29 ± 2.6 | 3.37 ± 0.97 | 7.58 ± 1.5 |
| R | 6.62 | 2.25 | 6.74 | 2.96 | 6.36 | 5.4 | 6.2 | 3.82 | 0.21 | 0.16 |

$Q_{24}$: Quantity of 17-B-estradiol or NETA released in 24 hours expressed as μg/cm²
$Q_0$: Initial quantity of 17-B-estradiol or NETA expressed as μg/cm²
R: Yield expressed as a percentage (R = 100 · $Q_{24}/Q_0$).

TABLE II

Comparison between ESTRAGEST ® and device according to the invention containing either 17-B-estradiol or NETA.

| | Ex 1 | Ex 2 | Ex 3 | Ex 4 | Ex 5 | EX 6 | Ex 7 | ESTRAGEST ® | |
|---|---|---|---|---|---|---|---|---|---|
| | NETA | NETA | NETA | Es | Es | Es | Es | Es | NETA |
| $Q_0$ | 400.3 | 400.4 | 400.8 | 200 | 200 | 205.4 | 200.2 | 1604 | 4740 |
| $Q_{24}$ | 27.34 ± 5,1 | 11.05 ± 2 | 10.26 ± 2,5 | 13.88 ± 2,7 | 13.91 ± 1,1 | 14.95 ± 2,6 | 8.73 ± 0.6 | 3.37 ± 0.97 | 7.58 ± 1.5 |
| R | 6.83 | 2.76 | 2.56 | 6.94 | 6.96 | 7.28 | 4.36 | 0.21 | 0.16 |

$Q_{24}$: Quantity of 17-B-estradiol or NETA released in 24 hours expressed in μg/cm²
$Q_0$: Initial quantity of 17-B-estradiol or NETA expressed in μg/cm²
R: Yield expressed as a percentage (100 · $Q_{24}/Q_0$)

TABLE III

Comparison between the devices according to the invention and the apparatus described in patent document FR-A-2-612 785.

| | CP1 | Ex 5 | Ex 6 | Ex 8 |
|---|---|---|---|---|
| $Q_0$ | 565 | 200 | 205.4 | 200 |
| $Q_{24}$ | 64.34 ± 20.8 | 43.65 ± 4.7 | 48.15 ± 2.6 | 41.8 ± 5.5 |
| $R_{24}$ | 11.4 | 21.8 | 24.1 | 20.9 |
| $Q_{48}$ | 137.4 ± 31.5 | 76.38 ± 7.5 | 89.52 ± 5.2 | 81.15 ± 9.8 |
| $R_{48}$ | 24.2 | 38.2 | 44.8 | 40.6 |

$Q_0$: initial quantity of 17-B-estradiol expressed in µg/cm$^2$
$Q_{24}$: quantity of 17-B-estradiol released in 24 hours, expressed in µg/cm$^2$
$Q_{48}$: quantity of 17-B-estradiol released in 48 hours, expressed in µg/cm$^2$
$R_{24}$: yield as a percentage at 24 hours
$R_{48}$: yield as a percentage at 48 hours

TABLE IV

Comparison between ESTRAGEST ® and the devices according to the invention containing 17-B-estradiol and/or NETA based on different EVA copolymers.

| | Ex 13 | | Ex 14 | | Ex 15 | | ESTRAGEST ® | |
|---|---|---|---|---|---|---|---|---|
| | Es | | NETA | | Es | NETA | Es | NETA |
| $Q_0$ | 190.3 | | 466.7 | | 192 | 291 | 1604 | 4740 |
| $Q_{24}$ | 11.04 ± 1.7 | | 16.8 ± 2.6 | | 12.9 ± 2.6 | 9.3 ± 2.6 | 3.37 ± 0.97 | 7,58 ± 1.5 |
| R | 5.8 | | 3.6 | | 6.72 | 3.2 | 0.21 | 0.16 |

$Q_0$: quantity of 17-B-estradiol and/or NETA expressed in µg/cm$^2$
$Q_{24}$: initial quantity of 17-B-estradiol and/or NETA released in 24 hours expressed in µg/cm$^2$
R: yield expressed as a percentage (100 · $Q_{24}/Q_0$).

We claim:

1. A self-adhesive transdermal matrix system for the administration by percutaneous route of a hormone, said system, which comprises a support and self-adhesive matrix, having a matrix consisting essentially of:
   (a) 40 to 60 parts by weight of an ethylene/vinyl acetate copolymer,
   (b) 5 to 20 parts by weight of a cellulose compound,
   (c) 35 to 55 parts by weight of at least one compound selected from the group consisting of:
   crotamiton,
   N-substituted 2-pyrrolidones of the formula I,

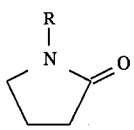

(I)

in which the R group represents a $(C_1-C_{15})$-alkyl, cyclohexyl or 2 - hydroxyethyl group, and higher $C_{12}-C_{20}$ aliphatic alcohols, and
   (d) 0.01 to 7 parts by weight of a hormone selected from the group consisting of estrogen compounds, progestogen compounds and mixtures thereof.

2. A system according to claim 1 wherein the higher aliphatic alcohol is 2-octyl-1-dodecanol.

3. A system according to claim 1 wherein the compound of the formula I is an N-alkyl-2-pyrrolidone, in which the alkyl group contains from 1 to 15 carbon atoms.

4. A system according to claim 1 wherein the ethylene/vinyl acetate copolymer has a vinyl acetate content of between 30 and 75% by weight with respect to the weight of said copolymer.

5. A system according to claim 1 wherein the hormone is an estrogen compound.

6. A system according to claim 1 wherein the hormone is a progestogen compound.

7. A system according to claim 1, wherein the hormone is a mixture consisting of an estrogen compound.

8. A system according to claim 1, wherein the matrix comprises, per total 100 parts by weight:
   (a) 46 parts by weight of EVA,
   (b) 10 parts by weight of ethylcellulose,
   (c1) 31.5 parts by weight of 2-octyl-1-dodecanol,
   (c2) 10.5 parts by weight of N-dodecyl-2-pyrrolidone, and
   (d) 2 parts by weight of 17-β-estradiol.

9. A system according to claim 1, wherein the matrix comprises, per total 100 parts by weight:
   (a) 45 parts by weight of EVA,
   (b) 10 parts by weight of ethylcellulose,
   (c1) 30.75 parts by weight of 2-octyl-1-dodecanol,
   (c2) 10.25 parts by weight of N-dodecyl-2-pyrrolidone, and
   (d) 4 parts by weight of norethisterone acetate.

10. A system according to claim 1 wherein the matrix comprises, per total 100 parts by weight:
    (a) 42 parts by weight of EVA,
    (b) 15 parts by weight of ethylcellulose,
    (c1) 28 parts by weight of 2-octyl-1-dodecanol,
    (c2) 10 parts by weight of N-dodecyl-2-pyrrolidone,
    (d1) 2 parts by weight of 17-β-estradiol, and
    (d2) 3 parts by weight of norethisterone acetate.

11. A method for preparing a transdermal matrix system according to claim 1, said method comprising the steps of:
    (α) mixing the EVA and the cellulose compound by stirring at a temperature higher than 110° C. to form a homogeneous mixture;
    (β) incorporating into the resulting homogeneous mixture, the hormone selected from the group consisting of estrogen compounds, progestogen compounds and mixtures thereof, under continued stirring at a temperature higher than 110° C., and homogenizing to form a further homogeneous mixture;
    (γ) coating the further homogeneous mixture onto a temporary anti-adherent support, at a temperature of between 100° and 140° C., in order to obtain a deposit of 50 to 300 g/m$_2$ on said support to form a matrix; and
    (δ) transferring the matrix thus obtained onto a final support.

12. A method for preparing a transdermal matrix system according to claim 1, said method comprising the steps of:
    (α) successively incorporating while stirring a compound selected from the group consisting of a higher aliphatic alcohol, crotamiton and an N-substituted 2-pyrrolidone of the formula I; the hormone selected from the group consisting of estrogen compounds, progestogen compounds and mixtures thereof; the EVA material; the cellulosic material and the chosen solvent to form a mixture;
    (β) stirring the mixture thus obtained at a temperature lower than the boiling point temperature of the solvent to form a homogeneous mixture;
    (γ) coating the homogeneous mixture onto a temporary anti-adherent support, at a temperature of between 50° and 70° C., to form a coating of 50 to 300 g/m$^2$ on said support;

(δ) heating the coating thus obtained to evaporate the solvent at a temperature of between 40° and 80° C. in accordance with the boiling point temperature of the solvent to form a dry matrix;

(ε) transferring the dry matrix thus obtained to a final support.

13. A system according to claim 3 wherein the compound of formula I is N-dodecyl-2-pyrrolidone.

14. A system according to claim 5, wherein the hormone is 17-β-estradiol.

15. A system according to claim 6, wherein the hormone is norethisterone acetate.

16. A method for preparing a transdermal matrix system according to claim 11, wherein step (β) further comprises the step of adding at least one compound selected from the group consisting of crotamiton and an aliphatic alcohol.

17. A method for preparing a transdermal matrix system according to claim 11, comprising the further step of incorporating into the resulting homogeneous mixture of step (β) the N-substituted 2-pyrrolidone(s) of formula 1, while stirring at a temperature below 110° C., and homogenizing.

18. A method for preparing a transdermal matrix system according to claim 8, said method comprising the steps of:

(α) mixing the EVA and the cellulose compound by stirring at a temperature higher than 110° C. to form a homogeneous mixture;

(β) incorporating into the resulting homogeneous mixture, the hormone selected from the group consisting of estrogen compounds, progestogen compounds and mixtures thereof, under continued stirring at a temperature higher than 110° C., and homogenizing to form a further homogeneous mixture;

(γ) coating the further homogeneous mixture onto a temporary anti-adherent support, at a temperature of between 100° and 140° C., in order to obtain a deposit of 50 to 300 g/m$_2$ on said support to form a matrix; and (δ) transferring the matrix thus obtained onto a final support.

19. A method for preparing a transdermal matrix system according to claim 18, wherein step (β) further comprises the step of adding at least one compound selected from the group consisting of crotamiton and an aliphatic alcohol.

20. A method for preparing a transdermal matrix system according to claim 18, comprising the further step of incorporating into the resulting homogeneous mixture of step (β) the N-substituted 2-pyrrolidone(s) of formula 1, while stirring at a temperature below 110° C., and homogenizing.

21. A method for preparing a transdermal matrix system according to claim 9, said method comprising the steps of:

(α) mixing the EVA and the cellulose compound by stirring at a temperature higher than 110° C. to form a homogeneous mixture;

(β) incorporating into the resulting homogeneous mixture, the hormone selected from the group consisting of estrogen compounds, progestogen compounds and mixtures thereof, under continued stirring at a temperature higher than 110° C., and homogenizing to form a further homogeneous mixture;

(γ) coating the further homogeneous mixture onto a temporary anti-adherent support, at a temperature of between 100° and 140° C., in order to obtain a deposit of 50 to 300 g/m$_2$ on said support to form a matrix; and (δ) transferring the matrix thus obtained onto a final support.

22. A method for preparing a transdermal matrix system according to claim 21, wherein step (β) further comprises the step of adding at least one compound selected from the group consisting of crotamiton and an aliphatic alcohol.

23. A method for preparing a transdermal matrix system according to claim 21, comprising the further step of incorporating into the resulting homogeneous mixture of step (β) the N-substituted 2-pyrrolidone(s) of formula 1, while stirring at a temperature below 110° C., and homogenizing.

24. A method for preparing a transdermal matrix system according to claim 10, said method comprising the steps of:

(α) mixing the EVA and the cellulose compound by stirring at a temperature higher than 110° C. to form a homogeneous mixture;

(β) incorporating into the resulting homogeneous mixture, the hormone selected from the group consisting of estrogen compounds, progestogen compounds and mixtures thereof, under continued stirring at a temperature higher than 110° C., and homogenizing to form a further homogeneous mixture;

(γ) coating the further homogeneous mixture onto a temporary anti-adherent support, at a temperature of between 100° and 140° C., in order to obtain a deposit of 50 to 300 g/m$_2$ on said support to form a matrix; and (δ) transferring the matrix thus obtained onto a final support.

25. A method for preparing a transdermal matrix system according to claim 24, wherein step (β) further comprises the step of adding at least one compound selected from the group consisting of crotamiton and an aliphatic alcohol.

26. A method for preparing a transdermal matrix system according to claim 24, comprising the further step of incorporating into the resulting homogeneous mixture of step (β) the N-substituted 2-pyrrolidone(s) of formula 1, while stirring at a temperature below 110° C., and homogenizing.

27. A method for preparing a transdermal matrix system according to claim 8, said method comprising the steps of:

(α) successively incorporating while stirring a compound selected from the group consisting of a higher aliphatic alcohol, crotamiton and an N-substituted 2-pyrrolidone of the formula I; the hormone selected from the group consisting of estrogen compounds, progestogen compounds and mixtures thereof; the EVA material; the cellulose compound and the chosen solvent to form a mixture;

(β) stirring the mixture at a temperature lower than the boiling point temperature of the solvent, to form a homogeneous mixture;

(γ) coating the homogeneous mixture onto a temporary anti-adherent support, at a temperature of between 50° and 70° C., so as to form a coating of 50 to 300 g/m$^2$ on said support;

(δ) heating the coating to evaporate the solvent at a temperature of between 40° and 80° C. in accordance with the boiling point temperature of the solvent to form a dry matrix;

(ε) transferring the dry matrix to a final support.

28. A method for preparing a transdermal matrix system according to claim 9, said method comprising the steps of:

(α) successively incorporating while stirring a compound selected from the group consisting of a higher aliphatic alcohol, crotamiton and an N-substituted 2-pyrrolidone of the formula I; the hormone selected from the group consisting of estrogen compounds, progestogen compounds and mixtures thereof; the EVA material; the cellulose compound and the chosen solvent to form a mixture;

(β) stirring the mixture at a temperature lower than the boiling point temperature of the solvent, to form a homogeneous mixture;

(γ) coating the homogeneous mixture onto a temporary anti-adherent support, at a temperature of between 50° and 70° C., so as to form a coating of 50 to 300 g/m$^2$ on said support;

(δ) heating the coating to evaporate the solvent at a temperature of between 40° and 80° C. in accordance with the boiling point temperature of the solvent to form a dry matrix;

(ε) transferring the dry matrix to a final support.

29. A method for preparing a transdermal matrix system according to claim 10, said method comprising the steps of:

(α) successively incorporating while stirring a compound selected from the group consisting of a higher aliphatic alcohol, crotamiton and an N-substituted 2-pyrrolidone of the formula I; the hormone selected from the group consisting of estrogen compounds, progestogen compounds and mixtures thereof; the EVA material; the cellulose compound and the chosen solvent to form a mixture;

(β) stirring the mixture at a temperature lower than the boiling point temperature of the solvent, to form a homogeneous mixture;

(γ) coating the homogeneous mixture onto a temporary anti-adherent support, at a temperature of between 50° and 70° C., so as to form a coating of 50 to 300 g/m$^2$ on said support;

(δ) heating the coating to evaporate the solvent at a temperature of between 40° and 80° C. in accordance with the boiling point temperature of the solvent to form a dry matrix;

(ε) transferring the dry matrix to a final support.

* * * * *